US012806227B2

(12) United States Patent
Zebda et al.

(10) Patent No.: US 12,806,227 B2
(45) Date of Patent: Nov. 24, 2026

(54) TRANSDERMAL DIHYDROGEN DELIVERY DEVICE

(71) Applicants: UNIVERSITE GRENOBLE ALPES, Saint Martin d'Heres (FR); CENTRE NATIONAL DE LA RECHERCHE SCIENTIFIQUE, Paris (FR); INSTITUT POLYTECHNIQUE DE GRENOBLE, Grenoble (FR); INSTITUT NATIONAL DE LA SANTE ET DE LA RECHERCHE MEDICALE, Paris (FR)

(72) Inventors: Abdelkader Zebda, Grenoble (FR); Philippe Cinquin, Saint Nazaire les Eymes (FR); Awatef Ben Tahar, Grenoble (FR); Véronique Coizet, Meylan (FR)

(73) Assignees: UNIVERSITE GRENOBLE ALPES, Saint Martin d'Heres (FR); CENTRE NATIONAL DE LA RECHERCHE SCIENTIFIQUE, Grenoble (FR); INSTITUT NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 558 days.

(21) Appl. No.: 18/554,315

(22) PCT Filed: Apr. 4, 2022

(86) PCT No.: PCT/EP2022/058903
§ 371 (c)(1),
(2) Date: Oct. 6, 2023

(87) PCT Pub. No.: WO2022/214439
PCT Pub. Date: Oct. 13, 2022

(65) Prior Publication Data

US 2024/0180958 A1 Jun. 6, 2024

(30) Foreign Application Priority Data

Apr. 8, 2021 (FR) ........................................ 2103592

(51) Int. Cl.
*A61K 33/00* (2006.01)
*A61M 37/00* (2006.01)
(Continued)

(52) U.S. Cl.
CPC ............. *A61K 33/00* (2013.01); *A61M 37/00* (2013.01); *A61N 1/0424* (2013.01);
(Continued)

(58) Field of Classification Search
CPC ..... A61K 33/00; A61M 37/00; A61N 1/0424; A61N 1/0428; A61N 1/0484;
(Continued)

(56) References Cited

U.S. PATENT DOCUMENTS 6,368,592 B1 4/2002 Colton et al.
6,468,499 B1 10/2002 Balachandran et al.
(Continued)

FOREIGN PATENT DOCUMENTS

WO 2019122441 A1 6/2019

OTHER PUBLICATIONS

Ge et al., Li, "Molecular hydrogen: a preventive and therapeutic medical gas for various diseases," Oncotarget, 2017, vol. 8, (No. 60), pp. 102653-102673.
(Continued)

*Primary Examiner* — Tasnim Mehjabin Ahmed
(74) *Attorney, Agent, or Firm* — HAUPTMAN HAM, LLP

(57) ABSTRACT

A transdermal dihydrogen delivery device including a body including an anode and a cathode, and an electrical energy source, wherein the body is based on a flexible material,
(Continued)

capable of shaping to the skin of a human or animal body, and the body includes a water receptacle, the relative arrangement of the receptacle, the anode and the cathode being configured such that the water contained in the receptacle is in contact with the anode and the cathode to form a closed electrical circuit, so as to produce dihydrogen at the cathode from the water taken from the receptacle, to release transdermally the dihydrogen produced. The proposed delivery device is relatively non-invasive, while allowing dihydrogen delivery.

15 Claims, 6 Drawing Sheets

(51) Int. Cl.

| | |
|---|---|
| ***A61N 1/04*** | (2006.01) |
| ***A61N 1/30*** | (2006.01) |
| ***C25B 1/04*** | (2021.01) |
| ***C25B 9/01*** | (2021.01) |
| ***C25B 9/17*** | (2021.01) |
| ***C25B 15/08*** | (2006.01) |

(52) U.S. Cl.
CPC ......... *A61N 1/0428* (2013.01); *A61N 1/0484* (2013.01); *A61N 1/0492* (2013.01); *A61N 1/303* (2013.01); *C25B 1/04* (2013.01); *C25B 9/01* (2021.01); *C25B 9/17* (2021.01); *C25B 15/08* (2013.01); *A61N 1/0448* (2013.01)

(58) Field of Classification Search
CPC .... A61N 1/0492; A61N 1/303; A61N 1/0448; C25B 1/04; C25B 9/01; C25B 9/17
See application file for complete search history.

(56) References Cited

U.S. PATENT DOCUMENTS

| | | | | |
|---|---|---|---|---|
| 9,005,187 | B2 | 4/2015 | Ziaie et al. | |
| 2009/0259171 | A1 | 10/2009 | Joshi et al. | |
| 2015/0112247 | A1 | 4/2015 | Tempelman et al. | |
| 2017/0105832 | A1 | 4/2017 | Rosenblum | |
| 2020/0030598 | A1 * | 1/2020 | Berman ................. | A61K 33/00 |
| 2020/0345992 | A1 * | 11/2020 | Safonov ............... | A61K 9/0014 |

OTHER PUBLICATIONS

Ichihara et al., Masatoshi, “Beneficial biological effects and the underlying mechanisms of molecular hydrogen—comprehensive review of 321 original articles -,” Medical Gas Research (2015) 5:12, pp. 1-21.

Ohno et al., Kinji, “Molecular Hydrogen as an Emerging Therapeutic Medical Gas for Neurodegenerative and Other Diseases,” Oxidative Medicine and Cellular Longevity, vol. 2012, Article ID 353152, pp. 1-12.

Ohta, Shigeo, “Recent Progress Toward Hydrogen Medicine: Potential of Molecular Hydrogen for Preventive and Therapeutic Applications,” Current Pharmaceutical Design, 2011, 17, pp. 2241-2252.

International Search Report and Written Opinion issued in corresponding International Application No. PCT/EP2022/058903, dated Jun. 20, 2022, European Patent Office, Rijswijk, Netherlands.

Chinese First Office Action issued in corresponding Chinese Application No. 202280028421.8, dated Mar. 21, 2026, pp. 1-15.

* cited by examiner

TRANSDERMAL DIHYDROGEN DELIVERY DEVICE

The present application is a U.S. National Phase of International Application Number PCT/EP2022/058903, filed Apr. 4, 2022, which claims priority to French Application No. 2103592, filed Apr. 8, 2021.

TECHNICAL FIELD OF THE INVENTION

The invention relates to the field of hydrogen therapy. It is particularly advantageously applied in the field of numerous conditions, and particularly inflammatory and/or oxidative stress-related conditions.

PRIOR ART

Hydrogen therapy is showing a growing benefit for treating a large number of conditions, particularly inflammatory and/or oxidative stress-related conditions. A review of more than 300 articles lists no less than 166 conditions for which dihydrogen delivery has been tested for its antioxidant properties (Ichihara, M., Sobue, S., Ito, M., Ito, M., Hirayama, M., & Ohno, K. (2015), "*Beneficial biological effects and the underlying mechanisms of molecular hydrogen-comprehensive review of* 321 *original articles", Medical gas research,* 5(1), 12).

Different techniques are known for administering dihydrogen to the human or animal body. Dihydrogen can be administered in the form of a gas for inhalation, formed by electrolysis. This technique is however expensive and inconvenient, as it requires complex respirator type equipment. Dihydrogen can be administered in the form of hydrogenated water, drunk by the patient.

These techniques show major limitations:

a small quantity of delivered dihydrogen, substantial variations in dihydrogen concentration, and a major constraint in terms of treatment compliance.

To avoid these drawbacks, dihydrogen can be produced by water electrolysis, carried out by a device implanted in the human or animal body. Document WO 2019/122441 A1 particularly discloses a device implantable in the human or animal body comprising an anode and a cathode electrically connected to an energy source. The device allows the passage of a bodily fluid acting as the electrolyte, making it possible to close the electric circuit. Dihydrogen is thus produced by electrolysis of water from a bodily fluid, inside the human body. The implantation of such a device remains very invasive for the patient, however.

Document US 2020/0030598 A1 discloses a delivery device of hydrogen, hydrogen peroxide and/or oxygen by electrolysis to be applied on the skin. The delivery of dihydrogen by the device remains limited, however.

An aim of the present invention is therefore that of providing a dihydrogen delivery device that is relatively non-invasive, and preferably non-invasive, for the human and animal body, while allowing sufficient, preferably enhanced, dihydrogen delivery.

The other aims, features and advantages of the present invention will become apparent upon examining the following description and the appended drawings. It is understood that other advantages can be incorporated therein.

SUMMARY OF THE INVENTION

To achieve this objective, according to one embodiment, a dihydrogen delivery device is provided comprising:

a body comprising at least one anode and at least one cathode, and an electrical energy source, the anode and the cathode being electrically connected to the electrical energy source.

The device being configured to deliver dihydrogen through the skin of a human or animal body:

the body is based on a flexible material, capable of shaping to the skin of a human or animal body, the body having an external surface comprising:

a bottom face intended to be applied on the skin and allowing the passage of dihydrogen, at least one face intended not to be in contact with the skin, the body comprises a water receptacle, the relative arrangement of the receptacle, the anode and the cathode being configured such that the water contained in the receptacle is in contact with the anode and the cathode to form a closed electrical circuit, so as to produce dihydrogen at the cathode from the water taken from the receptacle, to release transdermally the dihydrogen produced.

Thus, the device is capable of being applied on the skin of a human or animal body, the transdermal delivery makes it possible to minimise the impact on the body compared to implantable devices of the prior art.

Furthermore, the water receptacle comprised in the body and therefore capable of being considered as embedded, allows a dihydrogen delivery independent of a bodily fluid, for example sweat, to allow a delivery of a sufficient quantity of dihydrogen through the patient's skin. Indeed, this issue does not arise for implantable devices of the prior art, immersed in a bodily fluid capable of being used to produce dihydrogen.

The delivery device is therefore relatively non-invasive, and is preferably non-invasive, for the human or animal body, while making it possible to deliver a sufficient quantity of dihydrogen to obtain a beneficial effect on the body. Depending on the context of use, this quantity can for example vary from 1 μmol/hour to 40 μmol/hour. As dihydrogen is a rapidly diffused molecule, involving a low remanence at the release site thereof, the device is thus particularly adapted for the prevention and/or treatment of inflammatory and/or oxidative stress-related conditions in the vicinity of the skin of the human or animal body, such as diabetes, obesity, skin or surrounding tissue inflammation or psoriasis, skin cancer, vitiligo and any condition involving oxidative stress. The device can moreover be used for muscle recovery, against sore muscles for example.

A second aspect of the invention relates to an item of clothing comprising at least one dihydrogen delivery device according to the first aspect.

A third aspect of the invention relates to a dihydrogen delivery method comprising the application on the skin of a human or animal body, of the dihydrogen delivery device according to the first aspect of the invention, and an activation of the delivery device so as to deliver the dihydrogen transdermally.

As discussed hereinafter, according to one example, the transdermal dihydrogen delivery can be used for muscle recovery, for example against sore muscles. According to another example, the transdermal dihydrogen delivery is used for the prevention and/or treatment of conditions chosen from diabetes, obesity, inflammation, psoriasis, skin cancer, vitiligo and any condition involving oxidative stress.

BRIEF DESCRIPTION OF THE FIGURES

The aims, purposes, characteristics and advantages of the invention will be better understood upon reading the detailed description of one embodiment thereof, which is illustrated by means of the following accompanying drawings, in which.

Figure 1:
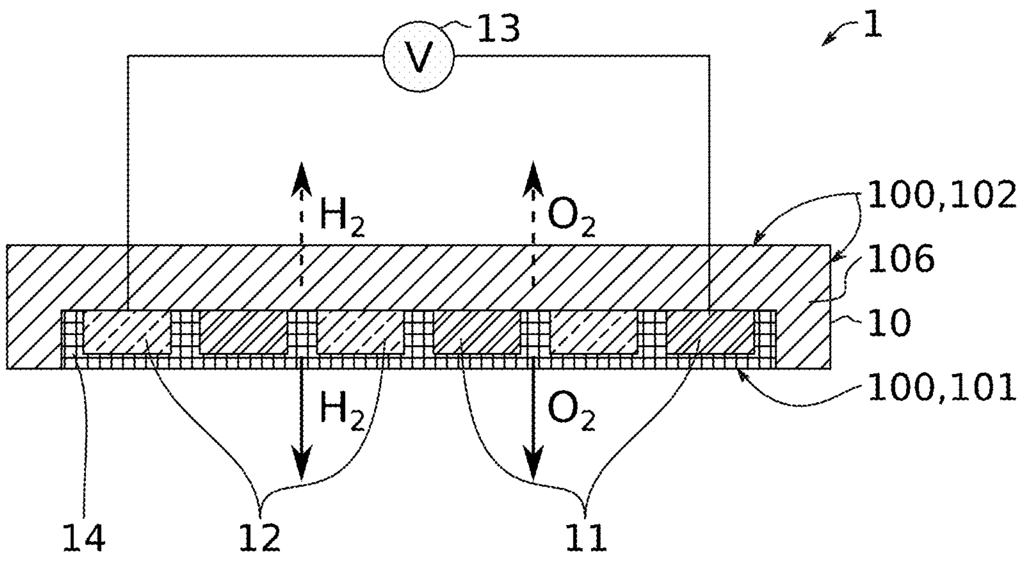
FIG. 1 represents a cross-sectional view of the delivery device according to one embodiment example.

The drawings are provided by way of example and are not intended to limit the scope of the invention. They constitute diagrammatic views intended to ease the understanding of the invention and are not necessarily to the scale of practical applications. In particular, the relative dimensions of the different elements making up the delivery device are not necessarily representative of reality.

DETAILED DESCRIPTION OF THE INVENTION

Before starting a detailed review of embodiments of the invention, optional features that may be used in combination or alternatively are set out hereinafter:

- the at least one cathode and the at least one anode are at least partially, and preferably entirely, disposed in the water receptacle,
- the at least one cathode and the at least one anode are in contact with a wall of the receptacle,
- the body is partially covered with a material non-permeable to dihydrogen forming at least one portion, for example a first portion, and preferably, the entirety, of the at least one face intended not to be in contact with the skin,
- the body is at least partially covered with a material having a cutoff threshold less than 1 μm, forming at least one portion, for example a second portion separate from the first portion, of the at least one face intended not to be in contact with the skin,
- the bottom face is at least partially, and preferably entirely, covered with a semi-permeable material having a cutoff threshold less than 1 μm,
- the bottom face is at least partially, and preferably entirely, covered with a semi-permeable material having a greater permeability to dihydrogen with respect to its permeability to dioxygen, preferably the semi-permeable material is permeable to dihydrogen and non-permeable to dioxygen,
- the bottom face is only partially covered with a non-permeable material to dihydrogen so as to form at least one opening not covered with the non-permeable material to dihydrogen,
- the at least one opening is covered with a semi-permeable material having a greater permeability to dihydrogen with respect to its permeability to dioxygen, preferably the semi-permeable material is permeable to dihydrogen and non-permeable to dioxygen,
- the bottom face is provided with at least one, and preferably a plurality of, microneedles intended to penetrate the skin,
- the bottom face being partially covered with a non-permeable material to dihydrogen so as to form at least one opening not covered with the non-permeable material to dihydrogen, the at least one microneedle is hollow and is disposed facing the opening,
- the water receptacle comprises, preferably is in the form of, a hydrogel. According to one example, the hydrogel is composed at least 95% by mass, and preferably at least 99% by mass of water,
- the cathode and the anode are disposed facing the bottom face intended to be in contact with the skin,
- the cathode and the anode form a stack, the cathode facing the bottom face intended to be in contact with the skin, and the anode facing a face intended not to be in contact with the skin,
- at least one from the cathode and the anode extend transversally in the receptacle so as to divide the receptacle into two separate parts, without water circulation between the two parts. According to one example, a first part communicates with the bottom face, and a second part communicates with a face intended not to be in contact with the skin,
- the bottom face being provided with at least one, and preferably a plurality of, microneedles intended to penetrate the skin, the cathode is formed by said microneedle. According one example, the cathode and the anode are each formed by a microneedle.

In the rest of the description, the term “on” does not necessarily mean “directly on”. Thus, when it is indicated that a part or a member A bears “on” a part or a member B, this does not mean that the parts or members A and B are necessarily in direct contact with the other. These parts or members A and B can either be in direct contact or bear on one another through one or more other part(s).

In the detailed description hereinafter, terms such as “transversal”, “top”, “bottom”, “internal”, “external” may be used. These terms must be interpreted relatively in relation to the normal position of use of the delivery device, once applied on the skin. For example, the term “bottom” corresponds to the faces or elements facing and/or in contact with the skin of the human or animal body whereon the device is intended to be applied. The term “top” corresponds to the faces or elements turned away from the skin of the human or animal body whereon the device is intended to be applied.

A parameter that is “substantially equal to/greater than/less than” a given value is understood to mean that this parameter is equal to/greater than/less than the given value, to within more or less 10%, or even to within 5%, of this value.

A “base” element of a material A is understood to mean an element comprising this material A and optionally other materials, for example additives.

The delivery device 1 is now described according to several embodiment examples illustrated by FIGS. 1 to 9.

As illustrated by FIG. 1, the device 1 comprises a body 10. The body 10 comprises electrodes: at least one anode 11 and at least one cathode 12, for the production of dihydrogen by water electrolysis. For this, the electrodes 11, 12 are connected to an electrical energy source 13. The electrical energy source 13 is only represented in FIG. 1 so as not to encumber the other figures.

The body 10 further comprises a water receptacle 14, so as to supply the water required for the closure of the electrical circuit with the electrodes 11, 12 and for the production of dihydrogen by electrolysis. In a manner known to a person skilled in the art, the electrodes 11, 12, the electrical energy source 13 and the water from the receptacle 14 forming a closed electrical circuit, the electrical energy source 13 supplies the circuit and sets a sufficient voltage to induce electrolysis of the water, with reduction of the water at the cathode to form dihydrogen, and oxidation of the water at the anode to form dioxygen, during the operation of the device.

The relative arrangement of the receptacle 14, the anode 11 and the cathode 12 is configured such that the water contained in the receptacle 14 is in contact with the anode 11 and the cathode 12 to form a closed electrical circuit. According to an example illustrated in FIG. 1, the anode and the cathode can partially enter, or be entirely included in the receptacle 14. According to another example illustrated in FIGS. 8A and 8B, the anode and/or the cathode can be directly in contact with a wall of the receptacle 14. The receptacle 14 can be delimited or formed from a material allowing water to pass through, such that the electrodes 11, 12 in contact with the water receptacle are in contact with the water.

The body 10 is capable of shaping to an external tissue of the human or animal body 3, for example an epithelium, to allow transdermal dihydrogen delivery. By external tissue, it is understood that the tissue forms an interface between the human body and the external environment thereof, such as for example the skin or the cornea. The body 10 is capable of shaping to the skin of a human or animal body 3. The body 10 is configured to have a sufficient flexibility to follow the contours of the human or animal body whereon it is applied. The body is based on one or more flexible materials. Preferably, the body 10 comprises at least one flexible material, such as polyethylene terephthalate, or an elastomer and more particularly a fluoroelastomer or a perfluoroelastomer (for example Viton™ marketed by Chemours, or Tecnoflon® marketed by Solvay). The outer surface 100 of the body 10 thus has a bottom face 101 intended to be applied on the skin, through which the dihydrogen delivery takes place. The device 1 thus enables transdermal dihydrogen delivery, without requiring an invasive operation such as implanting an electrolysis device in the body. Preferably, the bottom face 101 is intended to be entirely in contact with the skin. The outer surface 100 of the body 10 furthermore has at least one face 102 not intended to be applied on the skin, for example a top face and side faces.

During the development of the invention, it was indeed demonstrated that for some conditions or injuries, and particularly those affecting the skin or surrounding tissues such as fat tissues or muscles, cutaneous dihydrogen delivery is sufficient to relieve and/or treat the condition or injury. In order to ensure the delivery of a sufficient quantity of dihydrogen, the water receptacle 14 makes it possible to avoid electrolysis of a bodily fluid, and more particularly sweat.

Thus, the device can be presented in the form of a patch to be applied on the skin, extending mainly in a plane as illustrated by FIGS. 1 to 8B. According to an alternative or additional example, one or more delivery devices 1 can be comprised in an item of clothing 2 intended to be worn by a user. The item of clothing can be presented in the form of an armband or strip to surround for example the user's wrist, arm, leg, or forehead. According to the example illustrated in FIG. 9, the item 2 can be an armband comprising a plurality of devices 1, intended to be worn on the body 3 and more particularly around a user's arm. The item of clothing can be presented in the form of clothing, such as a t-shirt or a top, or underwear, preferably configured to mould the part of the body 3 to be treated, or indeed.

The device 1 extending mainly in a plane in order to limit impeding the user's movements. Preferably, the device has in this plane dimensions comprised between a centimetre (cm) and several tens of centimetres. Along a perpendicular direction to this plane, the device preferably has a dimension less than 5 cm, preferably less than 2 cm, and more preferably less than 1 cm. These dimensions are understood to mean with the energy source 13 when it is integrated in the body 10, or without the energy source 13 when it is offset.

The device 1 can be used in a dihydrogen delivery method. The delivery method comprises the application on the skin of a human or animal body, of the device 1, and the activation thereof so as to deliver the dihydrogen transdermally. The method can furthermore comprise the electrical connection of the device to the electrical energy source 13, particularly when it is offset from the body 10. The method can also comprise the control of the closure and opening of the electrical circuit formed by the means provided for this purpose.

According to the invention, animal can particularly be understood to mean large animals such as cattle, animals used in sports such as horses, pets such as dogs and cats, and laboratory animals such as rats, mice and monkeys.

The device 1 is now described in detail in relation to the different constituent elements thereof.

The receptacle 14 is configured, with the electrodes 11, 12, such that the electrodes are in contact with the water of the receptacle to form the closed electrical circuit. The receptacle can be in the form of a hollow receptacle delimited by a material and containing water. The material delimiting this material can be permeable to water, particularly when the electrodes 11, 12 are disposed in contact with the receptacle, such that the electrodes 11, 12 are in contact with the water from the receptacle 14 to produce dihydrogen.

According to an alternative or additional example, the receptacle can comprise, preferably be formed of, a porous material wherein the water is contained. For example, the porous material can be a sponge or a fabric. The porous material is preferably based on one or more polymers, such as polyacrylamide (PAAm), poly(p-phenyl-p-phthalamide), nanofibres of aramid, chitosan, or polyvinyl alcohol (PVA). According to a preferred example, the receptacle 14 comprises a hydrogel. According to one option, the receptacle 14 is formed by the hydrogel, the receptacle consists of the hydrogel. The term hydrogel is understood to mean a gel wherein the swelling agent is water. The matrix of a hydrogel is generally a network of one or more polymers. A hydrogel has the advantage of being flexible and having a large capacity to contain water. The hydrogen can be composed of at least 95%, and preferably at least 99% water, so as to maximise the quantity of water contained in the receptacle 14.

Preferably, the receptacle 14 has a height substantially between 0.5 cm and 5 cm. The height is measured along a perpendicular direction to the face of the body 10 intended to be applied on the skin. The height of the receptacle contributes to the definition of the water volume available for electrolysis and therefore the duration of use of the device. The height is also an important parameter for convenience of use and the aesthetic aspect when wearing the device. The choice of the height of the receptacle may therefore be made according to the target application and the location on the body on which the device is intended to be applied.

The water from the receptacle 14 forms a sufficiently conductive electrolyte to enable electrolysis of the water at the electrodes 11, 12. In a manner known to a person skilled in the art, this electrolyte contains for this salts comprising cations and anions such as Nat, $K^+$, $Ca^{2+}$, $Cl^-$ and $HCO^{3-}$.

The water receptacle 14 can be refillable, for example via an injection of water by a syringe into the receptacle 14. For this, the device 14 can comprise a tight opening, not shown in the figures, enabling communication between the receptacle 14 and the external surface 100 of the body 10. The tight opening comprises for example a seal through which a syringe can inject water to refill the receptacle 14. According to an alternative or additional example, the water receptacle 14 can be removably mounted in the device 1 to be replaceable. According to another example, the body 10 of the device 1 can be a consumable intended to be changed, particularly once the water from the receptacle 14 is used.

The body 10 of the device 1 can comprise an internal structural element 106 giving structure to the body 10 and imparting the pliability thereof. Preferably, the body 10 of the device is deformable under the pressure of a user's finger.

As illustrated in FIGS. 1 to 7, the body 10 is configured to receive the receptacle 14 in a hollow shape. This shape can for example be formed by the internal structural element 106, optionally in association with other elements of the body 10. The hollow shape is preferably facing, i.e. turned towards, the bottom face 101, wherein the receptacle 14 is placed. As illustrated in FIG. 1, the internal structural element 106 does not necessarily form a barrier to the gases produced by electrolysis.

The internal structural element 106, and any materials forming the external surface 100 of the body, described subsequently, are preferably electrically insulating. According to one example, the internal structural element 106 is based on or made of polymer such as polyethylene terephthalate (PET), poly(methylmethacrylate) (PMMA), polyamide, graphene, a photosensitive resin of SU-8 type, polyester, cellulose (for example a tattoo transfer paper).

The electrical energy source 13 can be integrated in the body 10 or be offset, i.e. disposed away from the body 10 of the device 1 and connected to the body 10 by electrical connections. The energy source can be:

- a battery, preferably a high energy density battery, for example a lithium battery,
- a mechanical energy recovery device, using for example the piezoelectric effect,
- a biological fuel cell capable of producing electricity by consuming chemical species, typically naturally present in the human or animal body, such as: glucose, carbohydrates, lipids, proteins,
- a solar energy recovery device, for example a photovoltaic module or a Grätzel cell,
- a thermal energy recovery device, for example a thermoelectric modules using the Seebeck effect.

The energy source 13 is preferably capable of producing a voltage substantially less than or equal to 1.4 V, in order to prevent the formation of $Cl_2$ from $Cl^-$ ions. The energy source 13 can be capable of producing a voltage substantially greater than 1.4 V, in order to increase the power of the device 1 and therefore the quantity of hydrogen delivered. To prevent a release of $Cl_2$ to the skin, the electrolyte in the receptacle 14 can be free from $Cl^-$ ions. Alternatively or additionally, a membrane can be configured to prevent the passage of $Cl_2$ produced, for example a membrane surrounding the receptacle 14, or a membrane on the bottom face 101 in contact with the skin, as described subsequently. A voltage booster or divider can be added to the energy source 14. Unless specified otherwise hereinafter, the supply from the energy source refers to its supply alone or in association with the voltage divider or booster. The power to produce one micromole of $H_2$/hour is substantially equal to or greater than 60 $\mu$W.

The device can furthermore comprise a voltage divider which makes it possible to obtain an electrolyser power supply voltage substantially less than or equal to 1.4 V. This is particularly useful when the power supply source 14 produces a voltage greater than 1.4 V. When there are several devices 1 or several pairs of cathodes 12 and anodes 11, the energy source 14 can be specific to each or shared.

Figure 2:
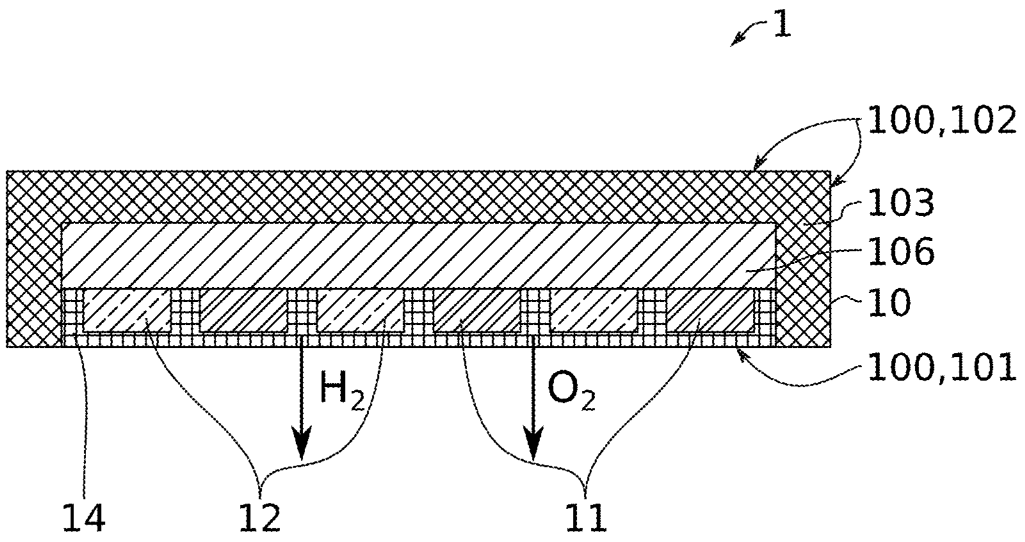
FIG. 2 represents a cross-sectional view of the delivery device according to another embodiment example wherein the device comprises a non-permeable material to dihydrogen.

According to one example, the external surface 100 is partially covered with, or in an equivalent way formed by, a non-permeable material 103 to dihydrogen 103 forming at least one portion 1020, and preferably the entirety, of the faces 102 of the body 10 intended not to be in contact with the skin. Thus, the diffusion of dihydrogen, or furthermore that of dioxygen, can be constrained in a plane or along a preferential direction, and particularly towards the skin, as illustrated by FIG. 2. Gaseous molecules are diffused particularly rapidly and in three dimensions with respect to other active substances. Constraining the diffusion thereof makes it possible to limit the loss of active substance during delivery, and thereof enhance the delivery of dihydrogen. This issue does not arise in prior art implanted devices, dihydrogen then being delivered to the body regardless of the delivery direction thereof. Note that if the material 103 is non-permeable to dihydrogen, the material will likewise be non-permeable to dioxygen.

The material non-permeable to dihydrogen 103 is preferably based on or made of one or more polymers chosen from:

- semi-crystalline thermoplastics, such as polyethylene, polyamide, polychlorotrifluoroethylene, polyetheretherketone (PEEK), polypropylene, chlorinated polyvinyl chloride (CPVC), polyvinyl chloride (PVC), and derivatives thereof,
- elastomers, such as polybutadiene, polychloroprene (for example Neoprene marketed by Nemours), ethylene and propylene terpolymers, ethylene and propylene copolymers, hydrogenated poly(butadiene-coacrylonitrile), poly(isobutylene-co-isoprene), silicone rubbers with various substituents on the polymer chain (for example phenyl, vinyl, and/or methyl), nitrile rubber, fluoroelastomers, or perfluoroelastomers for example:
  - vinylidene fluoride and at least one from hexafluoropropylene, tetrafluoroethylene, a fluorinated vinyl ether, propylene, ethylene,
  - fluoroelastomer of Viton™ type (polymer marketed by Chemours), perfluoroelastomers of Tecnoflon® type (polymer marketed by Solvay),
  - silicone rubbers having fluorinated substituent groups on the polymer chain (fluorosilicone rubber), Preferably, substantially at least 50%, preferably at least 70%, more preferably at least 90% and even more preferably the entirety of the faces 102 not intended to be applied on the skin is formed by the material non-permeable to dihydrogen 103. The more extensive the portion of the faces 102 formed by the non-permeable material to dihydrogen 103, the better the targeting of the dihydrogen produced, and therefore the greater the quantity of dihydrogen delivered to the skin.

According to one example, the bottom face 101 of the body can be covered or equivalently formed by a material in which the cutoff threshold makes it possible to modulate the species likely to pass through this face 101 of the device 1 to the skin and vice versa. According to one example illustrated in FIG. 3A, the bottom face 101 can be at least partially formed by a semi-permeable material 104 having a cutoff threshold less than 1 μm. Thus, this material 104 forms an antimicrobial barrier preventing any bacteria and/or microorganisms from the skin from entering the device 1, and more particularly the receptacle 14, while allowing the passage of dihydrogen and dioxygen. Indeed, water electrolysis inducing dioxygen production, the receptacle 14 is a medium conducive to microbial growth.

Figure 3A:
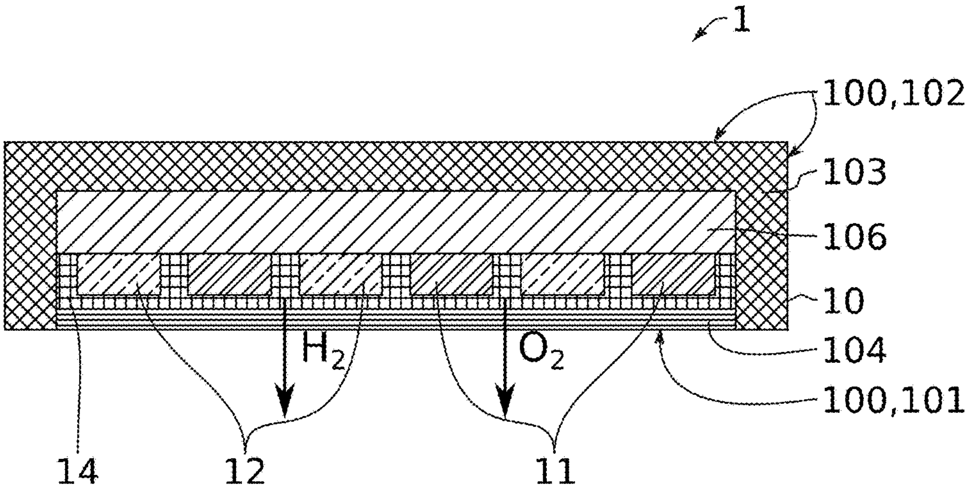
FIGS. 3A to 3C each represent a cross-sectional view of the delivery device according to several embodiment examples, wherein the bottom face is covered with a semi-permeable material.
Figure 3B:
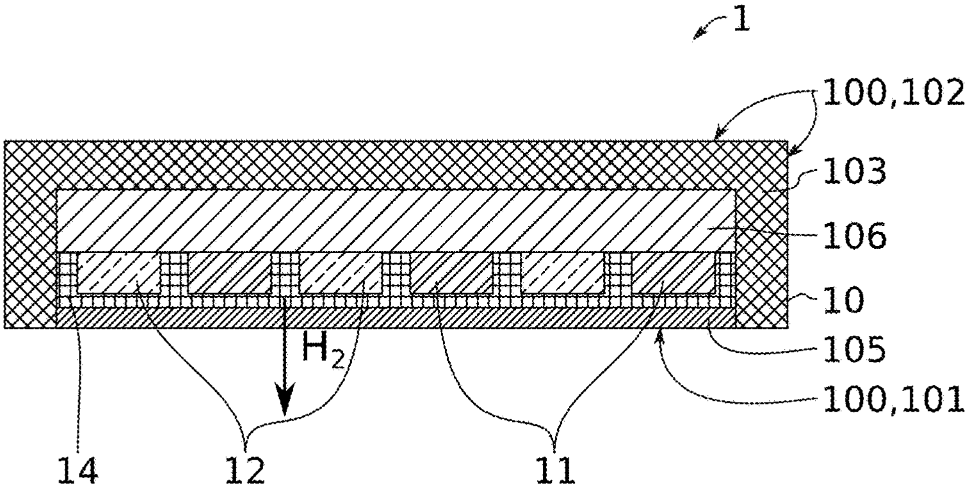
Figure 3C:
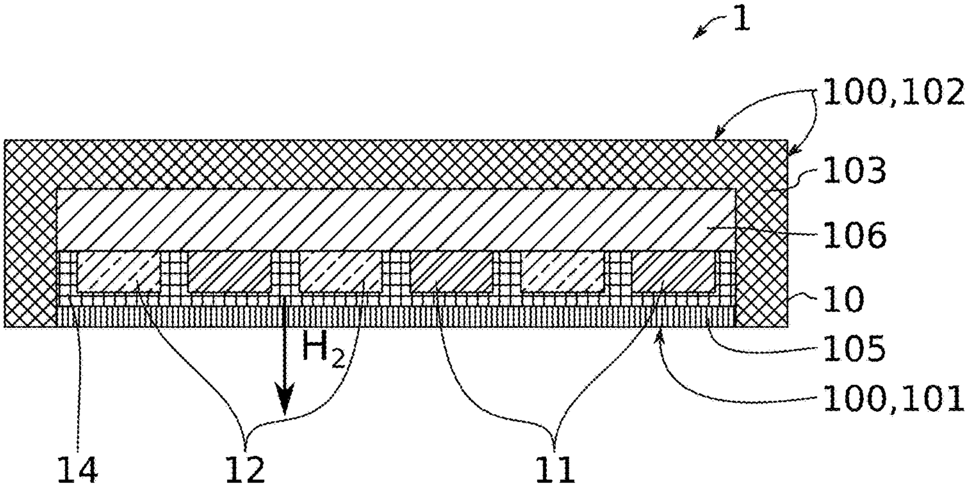

As illustrated for example in FIG. 3B, the bottom face 101 can be at least partially formed by a semi-permeable material 105 configured to favour the passage of dihydrogen with respect to dioxygen. According to one example, the semi-permeable material 105 has a greater permeability to dihydrogen than its permeability to dioxygen. According to one specific example, the semi-permeable material 105 is non-permeable to oxygen and is permeable to hydrogen. For this, the permeability of a material to a gas, and particularly of a polymer material, depends primarily, in a manner known to a person skilled in the art, on the cutoff threshold the material, the solubility of the gas in the material and the diffusion coefficient of the gas in the material. For example, the semi-permeable membrane 105 less permeable and preferably non-permeable to oxygen, and permeable to hydrogen can be a material with a permeability to oxygen less than or equal to $10^{-17}$ mol/(m·s·Pa) and a permeability to hydrogen greater than or equal to $10^{-14}$ mol/(m·s·Pa).

A person skilled in the art will know how to choose the suitable material for this purpose from existing materials in the art, and for example rubber, a photosensitive resin of SU-8 resin type, polyisobutylene such as Vistanex™ (manufactured by ExxonMobil Chemical). Thus, in addition to forming an antimicrobial barrier, the semi-permeable material prevents the passage of dioxygen produced at the anode through the bottom face 101 of the body 10. Only dihydrogen is delivered to the skin, which makes it possible to limit a reaction between dihydrogen and dioxygen in the patient's body and thus increase the quantity of dihydrogen delivered. Moreover, synergistically with the covering of the faces 102 with a non-permeable material to dihydrogen 103, dioxygen can be found trapped in the receptacle 14, which induces an increase in the pressure in the receptacle 14 and favours the passage of dihydrogen through the bottom face 101. According to one example, the material 105 has a cutoff threshold less than 32 Da.

The semi-permeable membrane 105 can be a semi-permeable membrane, for example based on or made of at least one polymer chosen from poly(ethylene terephthalate), and polycarbonate, according to the example illustrated in FIG. 3B. The semi-permeable membrane 105 can be a layer formed by a porous material, for example based on or made of at least one polymer chosen from poly(ethylene terephthalate), and polycarbonate, according to the example illustrated in FIG. 3C.

According to one example, the bottom face 101 can be partially covered with the non-permeable material to dihydrogen 103 so as to form at least one localised opening 1010 for dihydrogen passage. Thus, dihydrogen is only delivered to the skin at this or these opening(s) 1010, thus enhancing the targeting of dihydrogen on the skin. Preferably, each opening has a surface area substantially less than $1/5^{th}$, preferably $1/10^{th}$ of the total surface area of the bottom face 101.

Figure 4A:
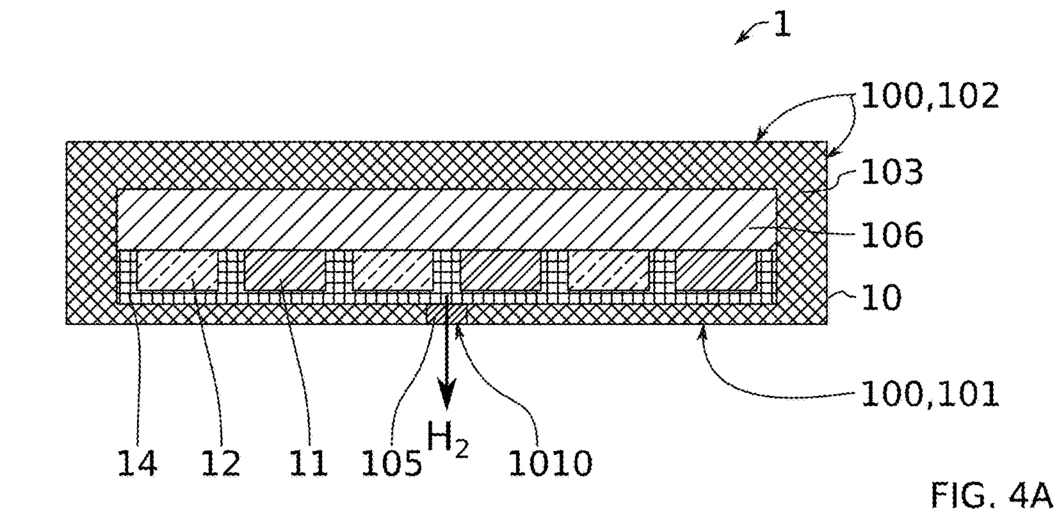
FIGS. 4A to 4C each represent a cross-sectional view of the delivery device according to several embodiment examples, wherein the device has one or more localised openings.
Figure 4B:
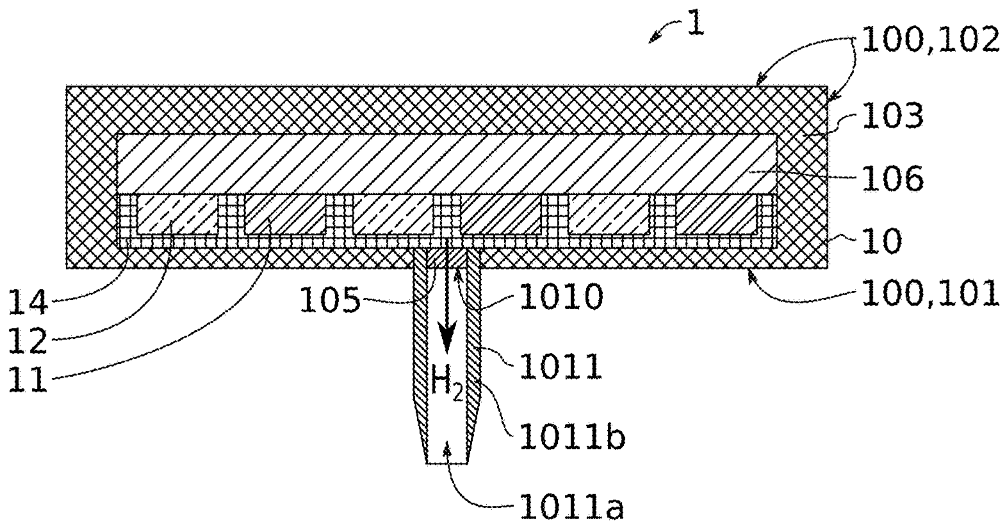
Figure 4C:
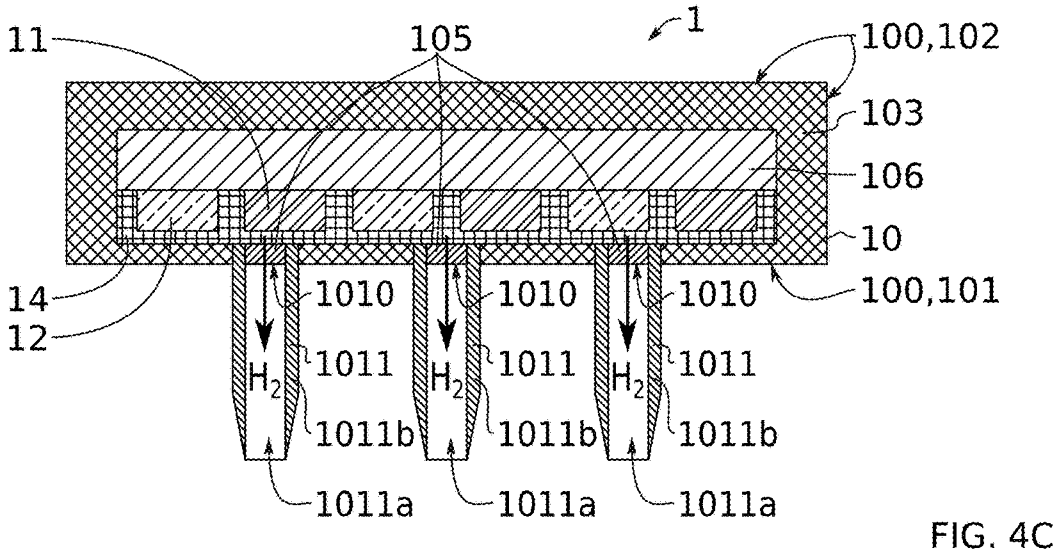

As illustrated by examples by FIGS. 4A to 4C, each of these openings 1010 can be covered with one of the materials 104, 105 described above, in which the cutoff threshold will then make it possible to modulate the species likely to pass through this opening 1010 from the device 1 to the skin and vice versa. According to the examples illustrated, the opening 1010 is covered with a semi-permeable material 105 having a greater permeability to dihydrogen with respect to its permeability to dioxygen, preferably permeable to dihydrogen and non-permeable to dioxygen, as described above, to favour the delivery of dihydrogen.

In addition to this opening, a hollow microneedle 1011 can be disposed at the opening 1010. The microneedle 1011 can comprise a micro-channel or hollow core opening on either side of the microneedle, along the main extension direction thereof. This microneedle 1011 is intended to penetrate the skin, as illustrated for example by FIG. 4B. The microneedle can comprise an external wall 1011*b* and a hollow central core 1011*a*, the external wall 1011*b* being disposed on either side of the localised opening, and the hollow central core 1011*a* communicating with the opening 1010. Thus the microneedle 1011 makes it possible to facilitate the contacting of the bottom face 101 of the body 10 on the skin, and limit the risk of detachment of the device 1. Furthermore, the microneedle 1011 being hollow, it makes it possible to facilitate the passage of dihydrogen through the skin surface. The microneedle comprises a through micro-channel ensuring the passage of dihydrogen from the body 10 to the skin and preferably at least through the upper layers of the epidermis. The bottom face 101 can have a plurality of openings 1010, for example forming a network of openings, each being capable of being equipped with a microneedle 1011.

Alternatively or additionally, it may be provided that the bottom face 101 has at least one, and preferably a plurality of solid or hollow microneedles intended to penetrate the skin, not disposed at an opening 1010, for example the bottom face 101 having no opening. Thus the microneedles facilitate the contacting of the bottom face 101 of the body 10 on the skin, and limit the risk of detachment of the device 1.

The microneedles described above can be based on or made of a rigid and biocompatible material. The rigid and biocompatible material can be a metal (for example made of titanium, nickel, a nickel iron alloy, gold, platinum or stainless steel) or a rigid polymer, such as polylactic acid, carboxymethylcellulose, polyglycolic acid, polyvinylpyrrolidone, polylactic glycolic acid. The microneedles are preferably of micrometric size, preferably less than 1.000 μm in length, and preferably less than 500 μm in width or diameter.

Alternatively or additionally, to help keep the body 10 of the device 1 in contact with the skin, it can be provided that at least one portion of the bottom face 101 comprise an adhesive layer, for example a glue. Alternatively or additionally, to help keep the body 10 of the device 1 in contact with the skin, it can be provided that the item of clothing 2 or that the device 1 comprise a holder configured to keep the body 10 in contact with the skin.

The cathode 12 and the anode 11 can be disposed facing the bottom face 101 intended to be in contact with the skin.

The electrodes can be disposed in the same plane substantially parallel with the bottom face 101. Thus, the delivery of all the gases produced by electrolysis on the skin is favoured, particularly when the electrodes are disposed on the internal structural element 106. According to a first example illustrated by FIGS. 1 to 4C, the electrodes 11, 12 can be disposed on a single face of the internal structural element 106, preferably facing the bottom face 101 and therefore turned towards the skin. The electrodes 11, 12 are then disposed facing the bottom face 101. Thus, the diffusion of the gases produced towards the bottom face 101, and therefore towards the skin, is favoured.

Figure 5:
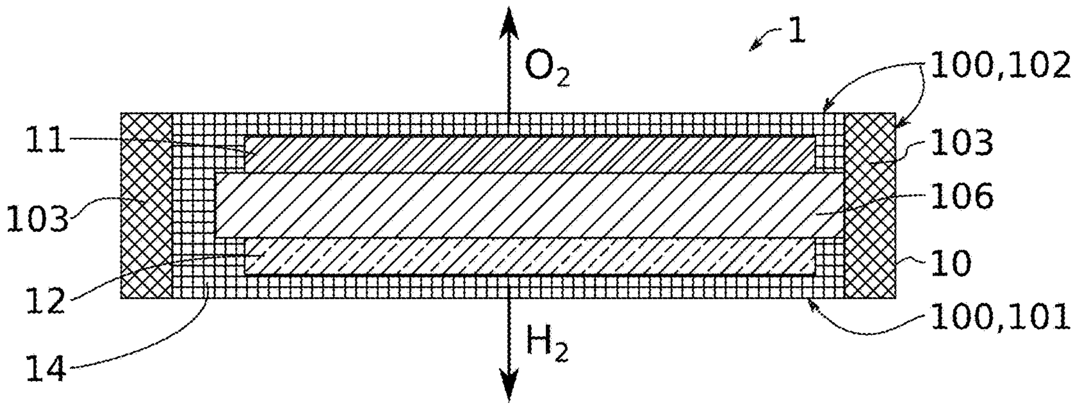
FIGS. 5, 6A and 6B each represent a cross-sectional view of the delivery device according to several embodiment examples, wherein the electrodes form a stack.
Figure 6A:
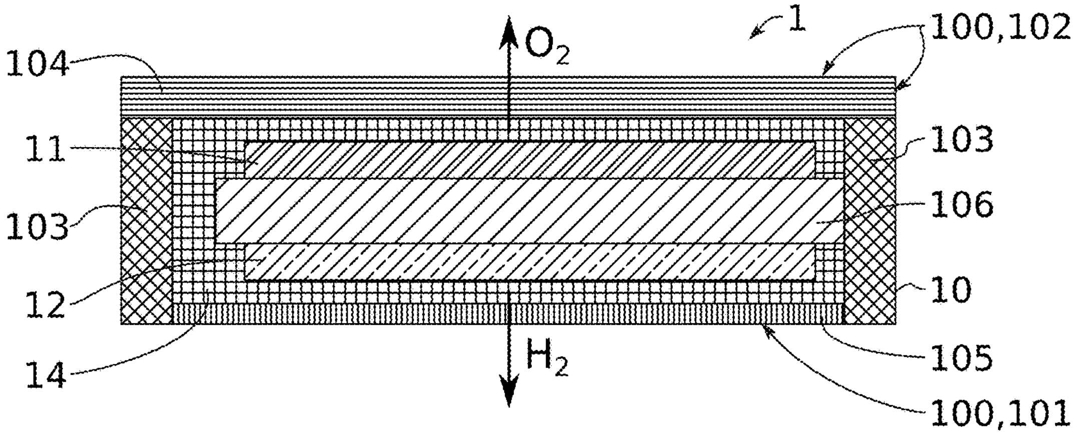
Figure 6B:
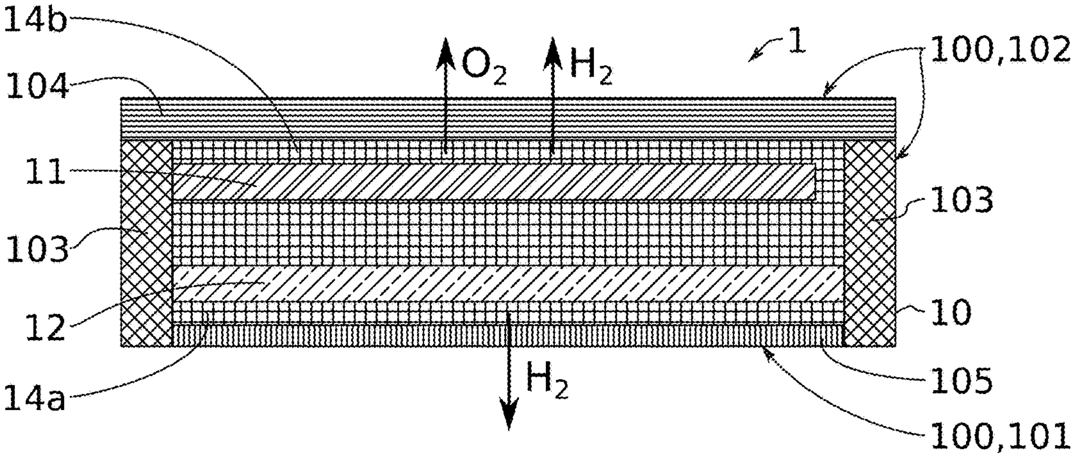
Figure 7:
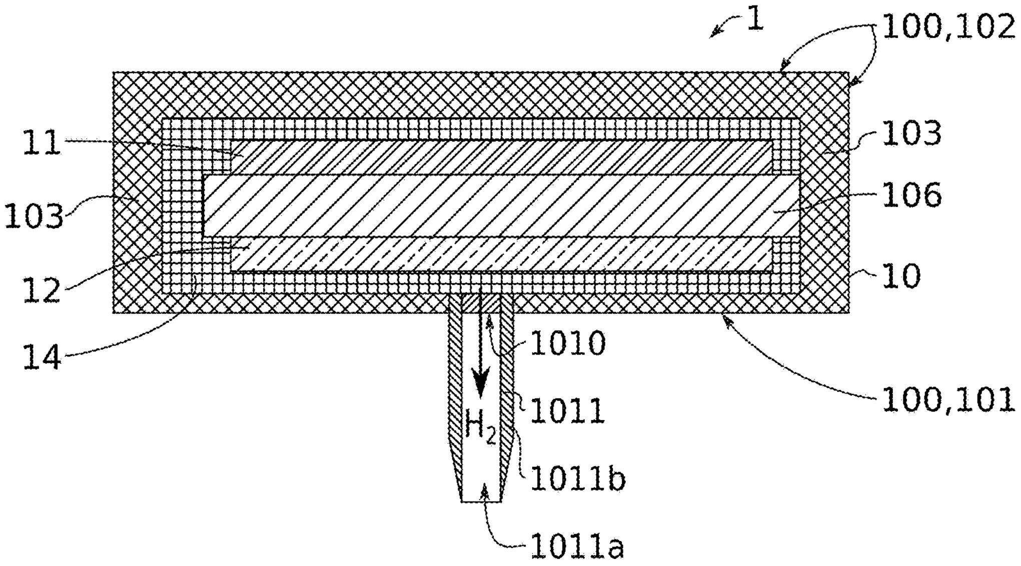
FIG. 7 represents a cross-sectional view of the delivery device according to another embodiment example.

According to a second example, illustrated by FIGS. 5 to 7, the cathode 12 and the anode 11 form a stack. The term stack is understood to mean that the electrodes are at least partially juxtaposed along a perpendicular direction to the face 101 intended to be in contact with the skin, without necessarily being directly in contact with one another. The cathode 12 is preferably facing the bottom face 101, and the anode 11 facing a face 102 intended not to be in contact with the skin, for example the top face 102. The cathode 12 is thus turned towards the bottom face 101, and the anode 11 is turned towards a face 102 intended not to be in contact with the skin, for example the top face 102. Thus, dioxygen is produced at the anode facing a face 102 intended not to be in contact with the skin, and dihydrogen is produced in the vicinity of the bottom face. The delivery of dihydrogen to the skin is favoured, with respect to that of dioxygen, to limit any reaction between these two gases and thus increase the quantity of dihydrogen delivered.

According to one example, illustrated in FIGS. 5, 6A and 7, the anode 11 can be disposed on one face of the internal structural element 106 and the cathode on one opposite face of this element 106. The internal structural element 106 can then extend transversally inside the receptacle 14, so as not to completely divide it into two separate parts, and allow water circulation in the receptacle 14. Alternatively or additionally, the internal structural element can for this have pores allowing this circulation.

According to one example illustrated by FIG. 6B, at least one electrode 11, 12 can extend transversally inside the receptacle 14, so as to divide it into two separate parts, with no water circulation between the two parts. Preferably, a first part 14*a* is then turned towards, preferably in contact with, the bottom face 101, whereas the second part 14*b* is turned towards, preferably in contact with a face 102 intended not to be in contact with the skin. The cathode 12 is preferably the electrode making this separation. Thus, the hydrogen produced in the first part 14*a* is necessarily transported by the bottom face to the skin, and does not escape via a face 102. The gases produced in the second part 14*b*, and therefore a portion of the dihydrogen and the dioxygen, escapes via the face 102. The face 102 can be covered with a material forming an antimicrobial barrier, as described above.

The top face 102 of the device may not be covered with a material limiting the diffusion of dioxygen, so as to facilitate the evacuation of dioxygen from the body 10, via a face 102 not in contact with the skin, as illustrated for example by FIG. 5. A face 102 not in contact with the skin, and preferably the top face 102, can be formed by a material having a cutoff threshold less than 1 μm, as described above, to form an antimicrobial barrier.

For the two examples described above, the electrodes 11, 12 are preferably disposed in the receptacle 14. According to one example, the electrodes 11, 12 can be in the form of terminals, bar or strip.

Figure 8A:
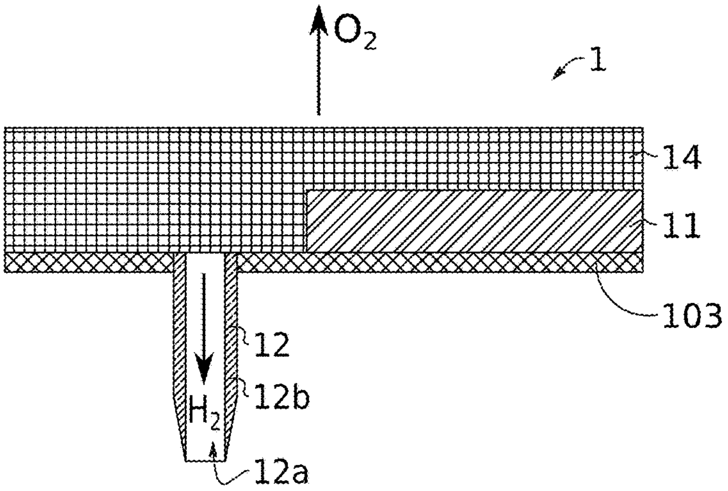
FIGS. 8A and 8B each represent a cross-sectional view of the delivery device according to several embodiment examples, wherein the electrodes are formed of microneedles intended to penetrate the skin.
Figure 8B:
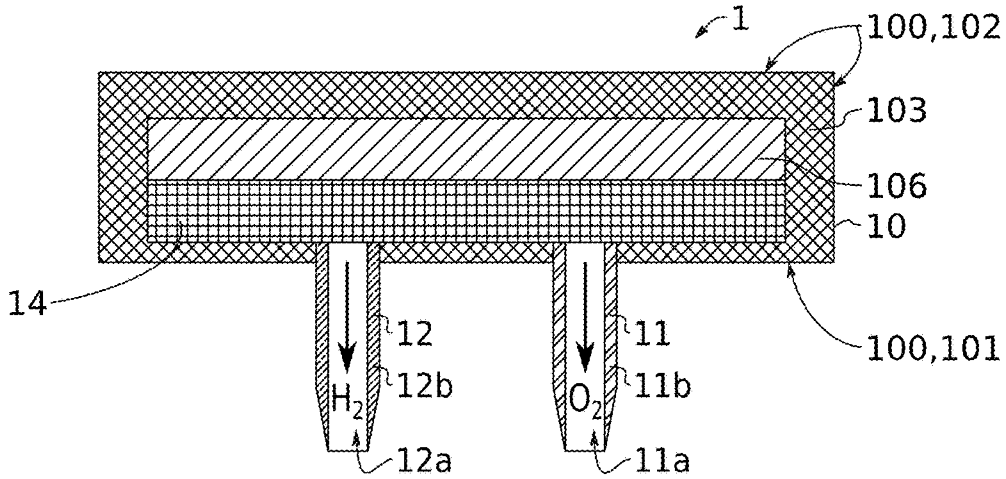
Figure 9:
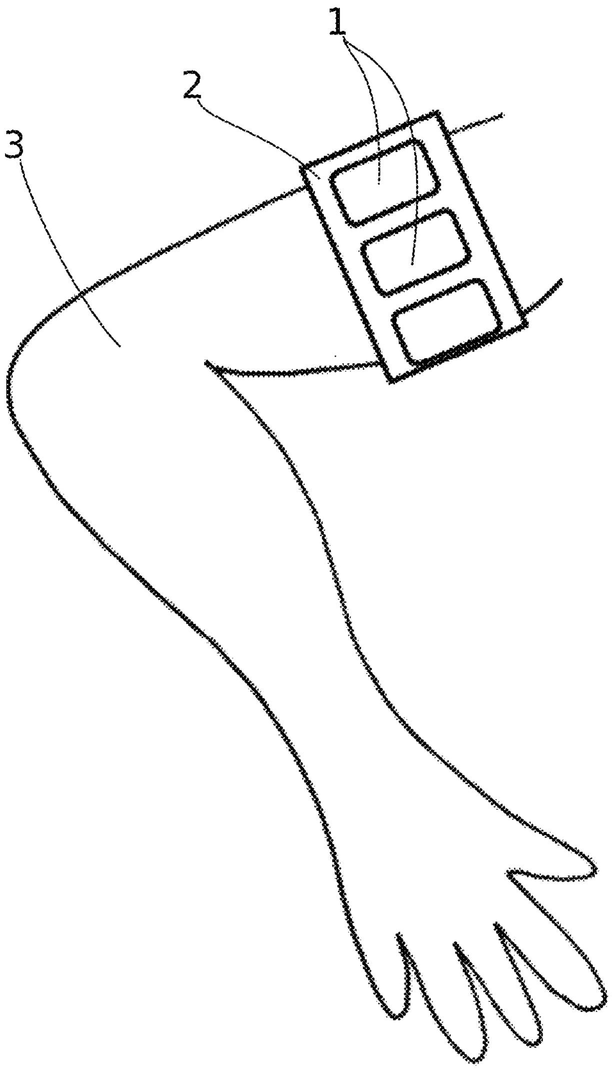
FIG. 9 represents an overall view of an armband comprising several dihydrogen delivery devices.

According to a third example, illustrated by FIGS. 8A and 8B, only the cathode 12 or the cathode 12 and the anode 11 can each be formed by a microneedle, preferably hollow, intended to penetrate the skin. The water from the receptacle 14 can for example by transported by capillarity in the hollow core 11*a*, 12*a* of the electrodes 11, 12 and electrolysis can be performed at the outer wall 11*b*, 12*b* thereof. Electrolysis is thus performed at the skin, enhancing the delivery of gases, and in particular dihydrogen, to the skin, while helping keep the body 10 of the device 1 in contact with the skin.

According to one or the other of the three examples above, the body 10 can preferably comprise several pairs of one cathode 12 and one anode 11, to form an electrode network. Thus, the surface area for producing gases by electrolysis is increased, to maximise the quantity of gas produced.

The electrodes can furthermore each be encapsulated by a semi-permeable membrane surrounding each electrode, for example of polyether sulfone, polyamide, polymethylmethacrylate (PMMA), chitosan, polyvinyl alcohol type.

When at least one or the electrodes 11, 12 is contained in the receptacle 14, the cathode(s) 12 can be separated from the anode(s) 11 by a proton exchange membrane or polymer electrolyte membrane (PEM), which is a semi-permeable membrane manufactured from ionomers allow proton conduction while being impermeable to gases such a dioxygen or dihydrogen. Protons pass through whereas gases are stopped. This feature is used in MEAs (Membrane Electrode Assembly) of PEM fuel cells and PEM electrolysers. PEMs are manufactured from pure polymer membranes or composite membranes where the materials form a polymer matrix. One of the most commonly used materials is Nafion, a fluorinated polymer produced by DuPont. The proton exchange membrane can divide the receptacle 14 into two parts. Thus, dihydrogen production can be isolated from dioxygen production in the body 10 of the device 1.

The composition of the electrodes is adapted to the function of each. They can be made of the same material or of two different materials. They can be based on or made of carbon. Preferably, the type of carbon material is chosen from graphite, carbon nanotubes, graphene, activated carbon or diamond. The material of the electrodes can be doped, particularly with platinum, iron or gold. The electrodes can be based on or made of platinum, gold, indium tin oxide (commonly abbreviated to ITO), iridium or doped diamond, in particular at least the anode can be made of gold, or doped with gold. The electrodes can have a thickness substantially between 100 μm and 2 mm, along a perpendicular direction to the face 101 intended to be in contact with the skin, particularly when the electrodes are in the form of terminals, bar or strip.

The features described above can be combined with each other to form new embodiment examples, as illustrated for example by FIG. 7.

We describe some specific cases hereinafter. In the light of the features described above, it is apparent for example that the device illustrated by FIG. 2 allows a delivery both of dihydrogen and dioxygen to the skin via the bottom face 101. The device illustrated by FIG. 3B or 3C makes it possible to deliver only the dihydrogen produced, dioxygen being trapped in the receptacle 14. The devices illustrated by FIGS. 4A to 4C allow a targeted delivery of dihydrogen via the opening(s) 1010, whereas dioxygen remains trapped in the receptacle 14. The device illustrated by FIG. 6A allows a favoured delivery of dihydrogen to the skin, most of the dioxygen being evacuated via the top face 102 of the body 10.

In the light of the above description, it is clear that the invention provides a dihydrogen delivery device that is relatively non-invasive, and preferably non-invasive, for the human and animal body, while enhancing dihydrogen delivery.

The invention is not limited to the aforementioned embodiments, and includes all the embodiments covered by the invention. The present invention is not limited to the examples described above. Many other alternative embodiments are possible, for example by combining features described above, without leaving the scope of the invention. Furthermore, the features described in relation to an aspect of the invention can be combined with another aspect of the invention.

LIST OF REFERENCE NUMBERS

1 Device
10 Body
100 External surface
101 Bottom face intended to be in contact with the skin
1010 Opening
1011 Microneedle
1011*a* Central core
1011*b* Wall
102 Face intended not to be in contact with the skin
103 Non-permeable material to dihydrogen
104 Material having a cutoff threshold less than 1 μm
105 Semi-permeable material to dihydrogen
106 Internal structural elements
11 Anode
11*a* Central core
11*b* Wall
12 Cathode
12*a* Central core
12*b* Wall
13 Electrical energy source
14 Water receptacle
2 Item of clothing
3 Human or animal body

The invention claimed is:

1. A dihydrogen delivery device comprising:

a body comprising at least one anode and at least one cathode; and an electrical energy source, the anode and the cathode being electrically connected to the electrical energy source;

the device being configured to deliver dihydrogen through skin of a human or animal body; wherein the body is based on a flexible material, capable of shaping to the skin of a human or animal body, the body having an external surface comprising:

a bottom face intended to be applied on the skin; and at least one face intended not to be in contact with the skin;

the body comprises a water receptacle, the relative arrangement of the receptacle, the anode and the cathode being configured such that the water contained in the receptacle is in contact with the anode and the cathode to form a closed electrical circuit, so as to produce dihydrogen at the cathode from the water taken from the receptacle, to release transdermally the dihydrogen produced;

wherein the body is partially covered with a non-permeable material to dihydrogen forming at least one portion of the at least one face intended not to be in contact with the skin; and wherein the bottom face is at least partially covered with a semi-permeable material having a greater permeability to dihydrogen with respect to a permeability to dioxygen.

2. The device according to claim 1, wherein, the body is at least partially covered with a material having a cutoff threshold less than 1 μm, forming at least one portion of the at least one face intended not to be in contact with the skin.

3. The device according to claim 1, wherein the semi-permeable material has a cutoff threshold less than 1 μm.

4. The device according to claim 1, wherein the bottom face is only partially covered with the non-permeable material to dihydrogen so as to form at least one opening not covered with the non-permeable material to dihydrogen.

5. The device according to claim 4, wherein the at least one opening is covered with the semi-permeable material.

6. The device according to claim 1, wherein the bottom face is provided with at least one microneedle intended to penetrate the skin.

7. The device according to claim 6, wherein, the bottom face being partially covered with the non-permeable material to dihydrogen so as to form at least one opening not covered with the non-permeable material to dihydrogen, the at least one microneedle is hollow and is disposed facing the at least one opening.

8. The device according to claim 1, wherein the water receptacle comprises a hydrogel.

9. The device according to claim 1, wherein the cathode and the anode are disposed facing the bottom face intended to be in contact with the skin.

10. The device according to claim 1, wherein the cathode and the anode form a stack, the cathode facing the bottom face intended to be in contact with the skin, and the anode facing the at least one face intended not to be in contact with the skin.

11. The device according to claim 10, wherein one from the cathode and the anode extend transversally in the receptacle so as to divide the receptacle into two separate parts, without water circulation between the two parts, a first part communicating with the bottom face, a second part communicating with the at least one face intended not to be in contact with the skin.

12. The device according to claim 1, wherein, the bottom face being provided with at least one microneedle intended to penetrate the skin, the cathode is formed by said microneedle.

13. An item of clothing comprising the dihydrogen delivery device according to claim 1.

14. A dihydrogen delivery method comprising applying on skin of a human or animal body, the dihydrogen delivery device according to claim 1, and activating said device so as to deliver dihydrogen through said skin.

15. A dihydrogen delivery device:

a body comprising at least one anode and at least one cathode; and an electrical energy source, the anode and the cathode being electrically connected to the electrical energy source;

the device being configured to deliver dihydrogen through skin of a human or animal body; wherein the body is based on a flexible material, capable of shaping to the skin of a human or animal body, the body having an external surface comprising:

a bottom face intended to be applied on the skin; and at least one face intended not to be in contact with the skin;

the body comprises a water receptacle, the relative arrangement of the receptacle, the anode and the cathode being configured such that the water contained in the receptacle is in contact with the anode and the cathode to form a closed electrical circuit, so as to produce dihydrogen at the cathode from the water taken from the receptacle, to release transdermally the dihydrogen produced;

the body is partially covered with a non-permeable material to dihydrogen forming at least one portion of the at least one face intended not to be in contact with the skin;

the bottom face is provided with at least one microneedle intended to penetrate the skin; and the bottom face being partially covered with the non-permeable material to dihydrogen so as to form at least one opening not covered with the non-permeable material to dihydrogen, the at least one microneedle is hollow and is disposed facing the at least one opening.

* * * * *